US009046350B2

(12) United States Patent
Lim

(10) Patent No.: US 9,046,350 B2
(45) Date of Patent: Jun. 2, 2015

(54) METHOD AND APPARATUS OF MEASURING PRECISE HIGH SPEED DISPLACEMENT

(71) Applicant: Hyundai Motor Company, Seoul (KR)

(72) Inventor: Jae-Young Lim, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 230 days.

(21) Appl. No.: 13/715,851

(22) Filed: Dec. 14, 2012

(65) Prior Publication Data

US 2014/0078518 A1 Mar. 20, 2014

(30) Foreign Application Priority Data

Sep. 20, 2012 (KR) .......................... 10-2012-0104344

(51) Int. Cl.
*G01B 11/14* (2006.01)
*G01B 11/24* (2006.01)
*G01B 11/16* (2006.01)
*G01N 3/06* (2006.01)
*G01N 3/30* (2006.01)

(52) U.S. Cl.
CPC ................ *G01B 11/14* (2013.01); *G01B 11/16* (2013.01); *G01N 3/068* (2013.01); *G01N 3/30* (2013.01); *G01N 2203/0012* (2013.01); *G01N 2203/0017* (2013.01); *G01N 2203/028* (2013.01); *G01N 2203/0286* (2013.01)

(58) Field of Classification Search
None
See application file for complete search history.

(56) References Cited

U.S. PATENT DOCUMENTS

| | | | | | |
|---|---|---|---|---|---|
| 3,120,780 | A | * | 2/1964 | Vodra et al. | 356/32 |
| 3,421,819 | A | * | 1/1969 | Thure et al. | 356/32 |
| 3,592,545 | A | * | 7/1971 | Paine et al. | 356/32 |
| 3,765,774 | A | * | 10/1973 | Petrohilos | 356/640 |
| 4,112,746 | A | * | 9/1978 | Itoh et al. | 73/789 |
| 4,841,779 | A | * | 6/1989 | Mitsuhashi et al. | 73/826 |
| 4,869,110 | A | * | 9/1989 | Kent et al. | 73/800 |
| 4,962,669 | A | * | 10/1990 | Gernhart et al. | 73/800 |
| 5,199,304 | A | * | 4/1993 | Ferguson | 73/800 |
| 5,404,132 | A | * | 4/1995 | Canty et al. | 340/686.2 |
| 5,448,362 | A | * | 9/1995 | Perchak | 356/638 |
| 5,568,259 | A | * | 10/1996 | Kamegawa | 356/625 |
| 5,684,596 | A | * | 11/1997 | Eslinger et al. | 356/614 |
| 6,460,418 | B1 | * | 10/2002 | Hiyoshi | 73/800 |
| 7,377,181 | B2 | * | 5/2008 | Christ et al. | 73/800 |

FOREIGN PATENT DOCUMENTS

| | | | | |
|---|---|---|---|---|
| JP | 63085329 | A | * | 4/1988 |
| JP | 05-302880 | A | | 11/1993 |
| JP | 09096597 | A | * | 4/1997 |
| JP | 10089950 | A | * | 4/1998 |
| JP | 2004157522 | A | | 6/2004 |
| JP | 2007051405 | A | | 3/2007 |
| JP | 2007145963 | A | | 6/2007 |
| KR | 10-2011-0041437 | A | | 4/2011 |

* cited by examiner

*Primary Examiner* — Gordon J Stock, Jr.
(74) *Attorney, Agent, or Firm* — Mintz Levin Cohn Ferris Glovsky and Popeo, P.C.; Peter F. Corless

(57) ABSTRACT

The present invention relates to a method and apparatus for measuring precise high speed displacement, and more particularly, to a method and apparatus for measuring precise high speed displacement, which measures displacement of a test specimen by using a uniform intensity laser line and by using differences in a laser transmission amount according to the deformation of the test specimen, and measures a strain rate of the test specimen such as high strength fiber or the like using a high speed tensile test.

12 Claims, 3 Drawing Sheets

METHOD AND APPARATUS OF MEASURING PRECISE HIGH SPEED DISPLACEMENT

CROSS-REFERENCE TO RELATED APPLICATIONS

This application claims priority under 35 U.S.C. §119 to Korean Patent Application No. 10-2012-104344, filed on Sep. 20, 2012, in the Korean Intellectual Property Office, the disclosure of which is incorporated herein by reference in its entirety.

BACKGROUND OF THE INVENTION

1. Field of the Invention

The present invention relates to a method and apparatus for measuring precise high speed displacement, and more particularly, to a method and apparatus for measuring precise high speed displacement, which measures a strain rate of a test specimen such as high strength fiber or the like using a high speed tensile test.

2. Description of the Related Art

In recent years, emission of exhaust gas causing an increase in fuel consumption and environmental pollution has become a social problem, and thus the importance of a vehicle weight reduction has increased, and for this reason, the development of polymer materials and component design using the polymer materials is being developed.

In addition, the application of the polymer materials is advantageous in terms of the vehicle weight reduction, and may secure price competitiveness of products because the production cost of polymer materials is low compared to the production cost of metallic materials. Therefore, the use of polymer materials, in the interior and exterior of vehicles has increased, and components which have been made of metal are being replaced with components made of high functional polymer materials as the high functional polymer materials are developed.

Moreover, a test method of evaluating crash safety performance of vehicle components is generally classified into a high speed crash test and a low speed crash test. Particularly, the high speed crash test is carried out at about 64 km/h, and the impact energy absorbing ability of a vehicle body and performance of safety equipment such as seat belts, air bags and the like for protecting passengers are evaluated.

Furthermore, because there is a limitation in absorbing impact energy by components made of polymer materials such as plastic materials or the like, the crash test primarily relates to evaluation of crash safety performance of a vehicle body made of steel metal. However, because impact energy absorbing ability of interior materials made of polymer materials, such as a cockpit module and a door trim, exerts a substantive effect on crash performance of vehicles, it is necessary to design components in consideration of dynamic behavior of the polymer materials. Data regarding dynamic behavior including non-linear behavior of high strength polymer materials, such as data regarding high speed tension or the like are required.

The high speed tensile test is a tensile test in which a strain rate is more than or equal to $100 \text{ s}^{-1}$. Precise measurement of a strain of a test specimen and measurement of stress is important when evaluating high speed physical properties of materials.

In the related art, two common methods are used for a high speed tensile test. FIG. 1 shows a high speed tensile test method using a conventional static universal tensile test system (MTS). Specifically, the material is deformed at a high speed by coupling a hydraulic server to the static universal tensile test system (MTS) to increase a speed of a piston which moves the test specimen 10.

Furthermore, the stain rate of the test specimen 10 is measured by using a displacement sensor such as a linear variable differential transformer (LVDT) mounted therein, or is measured by directly mounting a strain gauge 20 on the test specimen 10. However, minute displacement less than or equal to 1 mm cannot be measured because of external factors such as a slip of a grip portion at a high speed, a noise generation or the like.

FIG. 2 shows a high speed tensile test method using an apparatus called a Hopkins bar (or a Kolsky bar) including an input bar, an output bar, an impact bar and a test specimen. A shock wave is generated when the impact bar 50 is launched by a pneumatic device and collides with a flange, and the shock wave deforms the test specimen 10 between the input bar 30 and the output bar 40.

Furthermore, a stress strain rate of the test specimen 10 is obtained by using stress waves respectively measured at the input bar 30 and the output bar 40. When a slip of a grip portion occurs, accuracy of a strain rate measurement decreases. Particularly, when the test specimen 10 is a thin steel plate or high strength fiber which is a few micrometers thick, a transmitted waveform cannot be measured because of a reduction of a cross-sectional area of the test specimen 10.

SUMMARY OF THE INVENTION

The present invention has been made in an effort to provide a method and apparatus for measuring precise high speed displacement of a test specimen such as high strength fiber or the like, which have a high reaction speed and may precisely measure a strain using a laser having a laser line of substantially uniform intensity, unlike a method in the related art, which measures displacement using a straight propagation property of a laser or interferences of a laser.

An exemplary embodiment of the present invention provides a method of measuring precise high speed displacement, which measures displacement of a test specimen by using a uniform intensity laser line and by using differences in laser transmission according to deformation of the test specimen.

The uniform intensity laser line may be formed by defocusing a laser beam with a laser line generator. The test specimen may be fixed and deformed between a first bar and a second bar of a bar system. The laser transmission amount may be measured by a photodetector when the uniform intensity laser line is focused.

Another exemplary embodiment of the present invention provides an apparatus of measuring precise high speed displacement, including: a laser generating device configured to generate a laser beam; a first focus lens configured to focus the generated laser beam; a laser line generator configured to form a uniform intensity laser line by defocusing the focused laser beam; a bar system configured to adjust a transmission amount of the laser line according to deformation of a test specimen; a second focus lens configured to focus the laser line which is transmitted through the bar system; and a photodetector configured to measure the transmission amount of the focused laser line.

The bar system may include a first bar, and a second bar on which a target for shielding the laser line is mounted. The test specimen may be fixed and deformed between a first bar and a second bar of the bar system.

The method and the apparatus of the present invention may use a laser line with uniform intensity unlike a method in the related art, which measures displacement by using a straight propagation property of a laser and interferences of a laser or measures an amount of reflected light, thereby enabling a substantially precise displacement measurement and achieving a high response speed at a high speed.

In addition, in the related art it may be difficult to measure displacement by directly attaching a gauge to the test specimen or by using a stress wave since the high strength fiber used as a reinforcing material of reinforced plastic composites is a few micrometers in size. However, deformation of the test specimen of a few micrometers may be precisely measured according to the present invention.

Furthermore, when an internationally standardized high speed physical property test method does not exist, reliability of collision analysis may be improved by obtaining a reliable high speed tensile data, and there may be decrease in development time of the technology, in costs and active management against design changes of components may be implemented by securing in advance dynamic properties of new materials in the future.

DETAILED DESCRIPTION OF THE EMBODIMENTS

Figure 1:
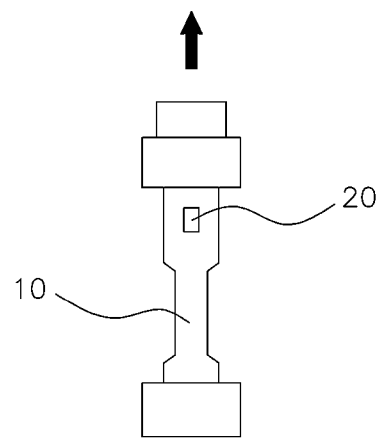
FIG. 1 is an exemplary view illustrating a high speed tensile test method using a general static universal tensile test system (MTS).

It should be understood that terms and words used in the specification and the accompanying claims are not to be construed as having common and dictionary meanings, but should be interpreted as having meanings and concepts corresponding to technical spirit of the present invention in view of the principle that the inventor can properly define the concepts of the terms and words in order to describe his/her own invention with the best method. Therefore, the embodiments described in the specification and the construction illustrated in the drawings are merely exemplary embodiments of the present invention and do not represent all the technical spirit of the present invention. It is to be understood that various equivalents and modifications can replace them at the time of filing the present application.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter, the present invention will be described in detail with reference to the accompanying drawings.

Figure 2:
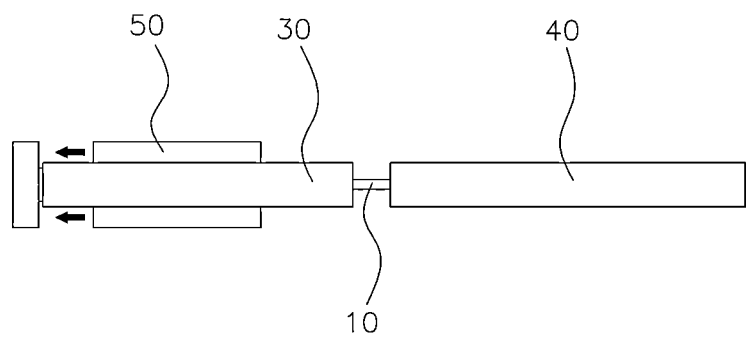
FIG. 2 is an exemplary view illustrating a high speed tensile test method using an apparatus called a Hopkins bar (or a Kolsky bar) including an input bar, an output bar, an impact bar and a test specimen.

As illustrated in FIG. 2, high speed displacement may be measured using a signal from an output bar 40 of a bar system in the related art, or as illustrated in FIG. 1, may be directly measured by attaching a strain gauge 20 to a test specimen 10. However, is the method illustrated in FIG. 1 may be ineffective because the test specimen 10 is broken after the test is completed.

Particularly, when a size and a strain of the test specimen 10 are a few micrometers, it may not be possible to use the signal from the output bar 40 or attach the strain gauge 20 to the test specimen 10, and thus, as an alternative to this method, a method of measuring displacement of the test specimen 10 by measuring a reflected amount of a laser beam, or by using interference is considered. However, because the above method may be sensitive to varying environment conditions and noise, the above method may not be effective for a high speed test which requires a high reaction speed.

Therefore, an object of the present invention is to solve the above-mentioned problem by measuring displacement of the test specimen 10 using a substantially uniform intensity laser line and using differences in laser transmission corresponding to deformation of the test specimen 10. A specific method and apparatus for carrying out the above method is described below.

Figure 3:
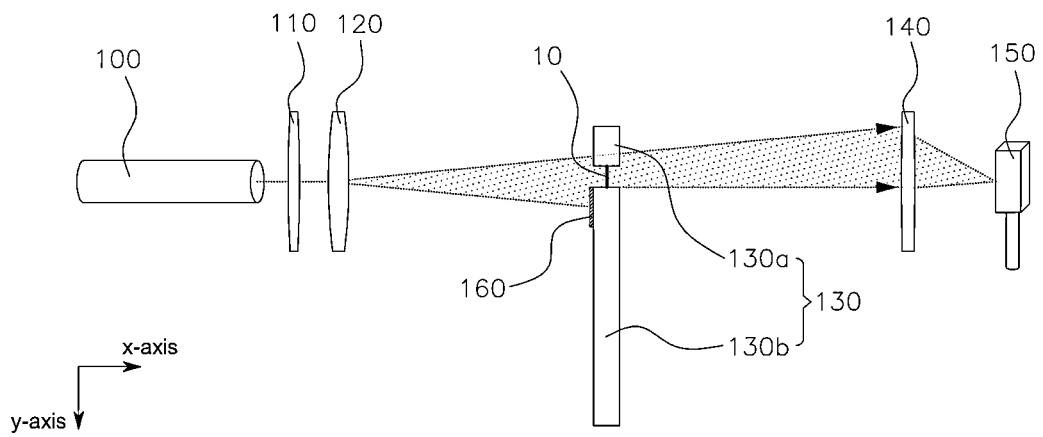
FIG. 3 is an exemplary schematic view of a precise high speed displacement measurement apparatus, according to an exemplary embodiment of the present invention.

FIG. 3 is an exemplary schematic view of a precise high speed displacement measurement apparatus, according to an exemplary embodiment of the present invention.

As shown in FIG. 3, the displacement measurement apparatus may include a laser generating device 100, a first focus lens 110, a laser line generator 120, a bar system 130 including a first bar 130a and a second bar 130b, a target 160, a second focus lens 140, and a photodetector 150.

The laser generating device 100 may generate a laser beam with a wavelength of about 670 nm, and a substantially high power (e.g., 100 mW) may be required to generate the laser beam. Furthermore, the first focus lens 110 may transmit the laser beam generated by the laser generating device 100 and focus the laser beam at a location. Moreover, the first focus lens 110 may reduce a spot size of the laser beam to less than or equal to about 1 mm.

The laser line generator 120 may defocus the focused laser beam to form a substantially uniform intensity laser line. The laser line illustrated in FIG. 3 refers to a laser line in a y-axis direction perpendicular to an x-axis direction which is an initial direction of the laser beam. The laser line may be formed to a thickness of about 1 mm and a width of about 30 mm on the bar system 130. According to an exemplary embodiment of the present invention, a Powell lens, which is a commonly used lens, may be used as the laser line generator 120.

Specifically, the bar system 130 may be configured to fix the test specimen 10, and may include the first bar 130a and the second bar 130b. Additionally, one of the first bar 130a and the second bar 130b may be a fixed bar, and the other may be a movable bar (e.g., in FIG. 3, the first bar 130a is a fixed bar, and the second bar 130b is a movable bar). In addition, the test specimen 10 may be fixed between the first bar 130a and the second bar 130b so as to be deformed, and the movable bar may be moved in the y-axis direction according to the deformation of the test specimen 10.

Moreover, the target 160 may shield the uniform intensity laser line formed by the laser line generator 120, and may be mounted on the movable second bar 130b. Alternatively, when the first bar 130a is a movable bar and the second bar 130b is a fixed bar, the target 160 may be mounted on the first bar 130a. In other words, the second bar 130b may be moved according to the deformation of the test specimen 10, and the target 160 mounted on the second bar 130b may be moved in the y-axis direction so a degree of shielding the laser line varies. Additionally, a transmission amount of the laser being transmitted through the bar system 130 may be linearly increased and decreased according to the deformation of the test specimen 10 due to the intensity of the laser line being substantially uniform.

Furthermore, second focus lens 140 may focus the laser line transmitted through the bar system 130 into a location on a sensing region of the photodetector.

The photodetector 150 may measure the laser transmission amount by converting the intensity of the laser line focused by the second focus lens 140 into an electric signal through the sensing region. To obtain a high response speed which is appropriate for a high speed test, the photodetector may be used with impedance matching (e.g., using a 50 ohm condenser) with a signal storage oscilloscope, and thereby, a high response speed (e.g., rise time) of up to about 1 ns may be obtained.

As described above, the laser beam generated by the laser generating device 100 may be transmitted through the first focus lens 110 and focused on the laser line generator 120. Thereafter, the laser line generator 120 may defocus the focused laser beam to form a uniform intensity laser line, and the defocused laser line may pass through the bar system 130. Differences in laser transmission amount may be caused when the target 160 mounted on the bar system 130 is moved according to the deformation of the test specimen 10, and the laser transmission amount is measured by the photodetector 150 when the uniform intensity laser line formed by the defocusing is focused by the second focus lens 140.

In other words, the displacement of the test specimen 10 in an axial direction (e.g., y-axis direction in FIG. 3) may be measured due to the intensity of the laser line being substantially uniform, and the laser transmission amount measured by the photodetector 150 having a linear relationship with the displacement of the test specimen 10.

Figure 4:
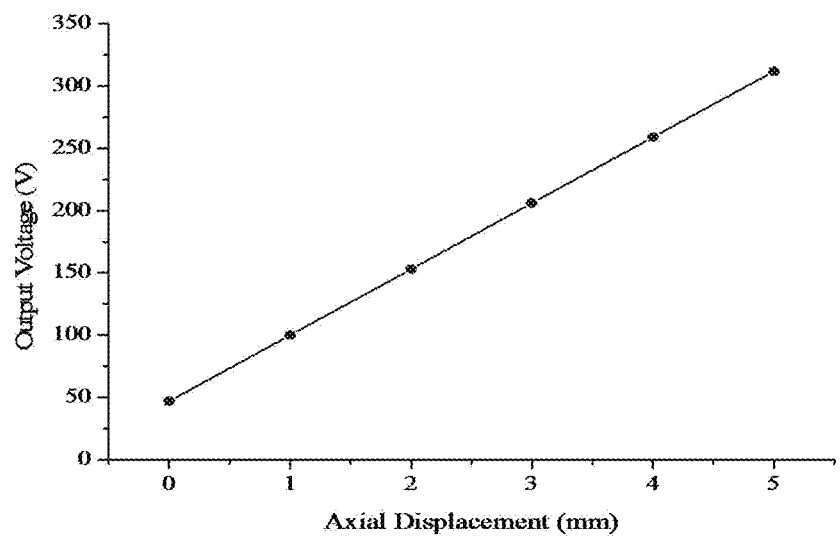
FIG. 4 is an exemplary graph illustrating data measured by converting the laser transmission amount measured by a photodetector corresponding to the displacement of a test specimen in the axial direction (y-axis direction) into an electric signal, according to an exemplary embodiment of the present invention.

FIG. 4 is an exemplary graph measured by converting the laser transmission amount measured by the photodetector according to the deformation of the test specimen in the axial direction (e.g., y-axis direction) into an electric signal. As shown, it may be known that the displacement of the test specimen 10 in the axial direction and the laser transmission amount detected by the photodetector 150 have a linear relationship to each other. Thus, the displacement of the test specimen 10 may be measured using differences in a laser transmission amount detected by the photodetector 150.

Figure 5:
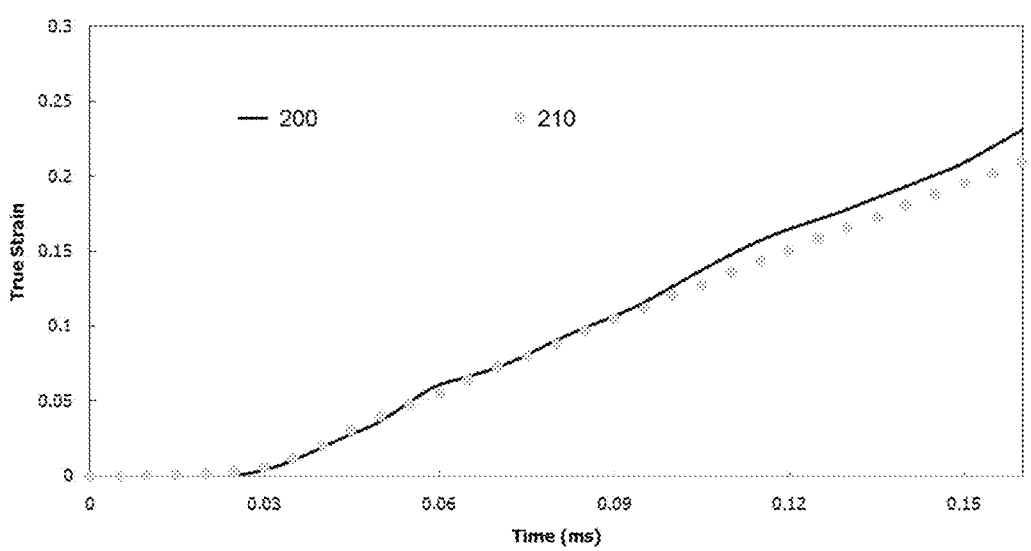
FIG. 5 is an exemplary graph comparing a strain rate of a test specimen measured according to an exemplary embodiment of the present invention with a strain rate of a test specimen measured by directly attaching a strain gauge to the test specimen.

FIG. 5 is an exemplary graph comparing a strain rate of a test specimen measured according to the present invention with a strain rate of a test specimen measured by directly attaching a strain gauge to the test specimen. As shown, it may be known that the graph line 200 showing a displacement measured with time by directly attaching the strain gauge 20 to the test specimen 10 is very similar to the graph line 210 showing a displacement measured with time according to the present invention.

Thus, the displacement of the test specimen 10 may be measured in a substantially precise high speed by the above described method and apparatus, and the present invention may obtain reliable tensile data using a high speed tensile test for a high strength fiber or the like.

While the present invention has been described in terms of specific embodiments of the present invention, which are merely exemplary embodiments, it should be appreciated that the present invention is not limited to those embodiments. The described embodiments may be changed or altered by the person skilled in the art without departing from the scope of the present invention, and various changes and alternations may be made within the equivalent range of the technical spirit of the present invention and the accompanying claims.

What is claimed is:

1. A method of measuring a high speed displacement of a test specimen, the method comprising:
    generating, by a laser beam generator, a laser beam; focusing, by a first focus lens, the generated laser beam;
    forming, by a laser line generator, a laser line having uniform intensity by defocusing the focused laser beam;
    adjusting, by a bar system, a transmission amount of the laser line according to a deformation of the test specimen;
    focusing, by a second focus lens, the laser line transmitted through the bar system; and
    measuring, by a photodetector, the transmission amount of the focused laser line.

2. The method of claim 1, wherein the test specimen is fixed and deformed between a first bar and a second bar of the bar system.

3. The method of claim 2, wherein the first bar is fixed and the second bar is movable.

4. The method of claim 2, further comprising shielding the laser line by a target mounted on the second bar.

5. The method of claim 1, wherein the laser line has a thickness of about 1 mm and a width of about 30 mm.

6. The method of claim 1, further comprising generating, by the laser beam generator, the laser beam having a wavelength of about 670 nm.

7. An apparatus of measuring a high speed displacement, comprising:
    a laser beam generator, configured to generate a laser beam; a first focus lens, configured to focus the generated laser beam;
    a laser line generator, configured to form a laser line having uniform intensity by defocusing the focused laser beam;
    a bar system, configured to adjust a transmission amount of the laser line according to deformation of a test specimen;
    a second focus lens, configured to focus the laser line transmitted through the bar system; and
    a photodetector, configured to measure the transmission amount of the focused laser line.

8. The apparatus of claim 7, wherein the bar system comprises:
    a first bar; and
    a second bar on which a target for shielding the laser line is mounted.

9. The apparatus of claim 7, wherein the test specimen is fixed and deformed between the first bar and the second bar of the bar system.

10. The apparatus of claim 8, wherein the first bar is fixed and the second bar is movable.

11. The apparatus of claim 7, wherein the laser line has a thickness of about 1 mm and a width of about 30 mm.

12. The apparatus of claim 7, wherein the laser beam generated by the laser beam generator has a wavelength of about 670 nm.

* * * * *